(12) United States Patent
Paz

(10) Patent No.: US 10,617,843 B2
(45) Date of Patent: *Apr. 14, 2020

(54) SYSTEMS AND METHODS FOR REMOVAL OF URINE

(71) Applicant: FlowSense Ltd., M.p. Misgav (IL)

(72) Inventor: Ilan Paz, Gush Etzion (IL)

(73) Assignee: FLOWSENSE LTD., M.p. Misgav (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/583,452

(22) Filed: May 1, 2017

(65) Prior Publication Data

US 2017/0232227 A1 Aug. 17, 2017

Related U.S. Application Data

(63) Continuation of application No. 14/037,371, filed on Sep. 26, 2013, now Pat. No. 9,687,628, which is a
(Continued)

(30) Foreign Application Priority Data

Jul. 16, 2007 (IL) .......................... 184632
Jul. 13, 2008 (IL) .......................... 192774

(51) Int. Cl.
*A61M 27/00* (2006.01)
*A61M 25/00* (2006.01)
(Continued)

(52) U.S. Cl.
CPC .......... *A61M 25/0017* (2013.01); *A61F 5/451* (2013.01); *A61M 1/0019* (2013.01);
(Continued)

(58) Field of Classification Search
CPC .......... A61M 25/0017; A61M 25/0021; A61M 1/0019; A61M 25/0043; A61M 39/08;
(Continued)

(56) References Cited

U.S. PATENT DOCUMENTS

| | | | | |
|---|---|---|---|---|
| 3,861,396 A | * | 1/1975 | Vaillancourt | A61F 5/441 604/129 |
| 3,902,492 A | * | 9/1975 | Greenhalgh | A61M 1/0084 604/43 |
| 3,955,574 A | * | 5/1976 | Rubinstein | A61M 1/0062 604/120 |
| 4,584,998 A | * | 4/1986 | McGrail | A61M 16/04 128/207.15 |
| 4,984,457 A | | 1/1991 | Morris | |

(Continued)

FOREIGN PATENT DOCUMENTS

| | | |
|---|---|---|
| CN | 2168601 Y | 6/1994 |
| CN | 1104920 A | 7/1995 |

OTHER PUBLICATIONS

Colas, Andre, and Jim Curtis. Silicone Biomaterials: History and Chemistry & medical Applications of Silicones. 2nd. Elsevier, Incorporated, 2005. 669, 705. Print.*

(Continued)

*Primary Examiner* — Andrew J Mensh
(74) *Attorney, Agent, or Firm* — Greer, Burns & Crain Ltd.

(57) ABSTRACT

An arrangement adapted for enhanced continuous flow of urine in a catheterized patient, the arrangement comprising a catheter tube having an inner diameter of less than six millimeters, said tube having an inner surface which is hydrophobic at least along a first segment thereof and being adapted to provide a continuously negative fluid pressure therein.

16 Claims, 5 Drawing Sheets

Related U.S. Application Data continuation of application No. 12/669,494, filed as application No. PCT/IL2008/000986 on Jul. 16, 2008, now Pat. No. 8,568,387.

(51) Int. Cl.
*A61M 1/00* (2006.01)
*A61F 5/451* (2006.01)
*A61M 39/28* (2006.01)
*A61M 39/08* (2006.01)

(52) U.S. Cl.
CPC .... *A61M 25/0021* (2013.01); *A61M 25/0045* (2013.01); *A61M 39/28* (2013.01); *A61M 25/0043* (2013.01); *A61M 39/08* (2013.01); *A61M 2025/0047* (2013.01); *A61M 2202/0496* (2013.01); *A61M 2205/0216* (2013.01); *A61M 2209/082* (2013.01)

(58) Field of Classification Search
CPC .. A61M 2025/0047; A61M 2202/0496; A61M 2209/082
USPC ............... 604/544, 177, 178, 43, 120, 151; 600/574, 575; 128/207.14
See application file for complete search history.

(56) References Cited

U.S. PATENT DOCUMENTS

| | | | |
|---|---|---|---|
| 5,251,639 | A | 10/1993 | Rentsch |
| 6,729,334 | B1* | 5/2004 | Baran ............... A61M 16/0463 128/200.14 |
| 6,793,651 | B1 | 11/2004 | Bennett et al. |
| 7,094,220 | B2* | 8/2006 | Tanghoj .................... A61F 5/44 604/177 |
| 2003/0018322 | A1 | 1/2003 | Tanghoj |
| 2006/0271019 | A1* | 11/2006 | Stoller ...................... A61F 5/44 604/544 |
| 2008/0027414 | A1 | 1/2008 | Tanghoj et al. |

OTHER PUBLICATIONS

Chinese Office Action from corresponding CN Application No. 201310521657.8, dated Dec. 11, 2014.
IPER for PCT/IL2008/000986, issued Jan. 19, 2010.
Written Opinion for PCT/IL2008/000986, dated Jan. 16, 2010.
Colas et al., "Silicone Biomaterials: History and Chemistry & Medical Applications of Silicones," Reprinted from Biomaterials Science, 2nd Edition, 2005.

* cited by examiner

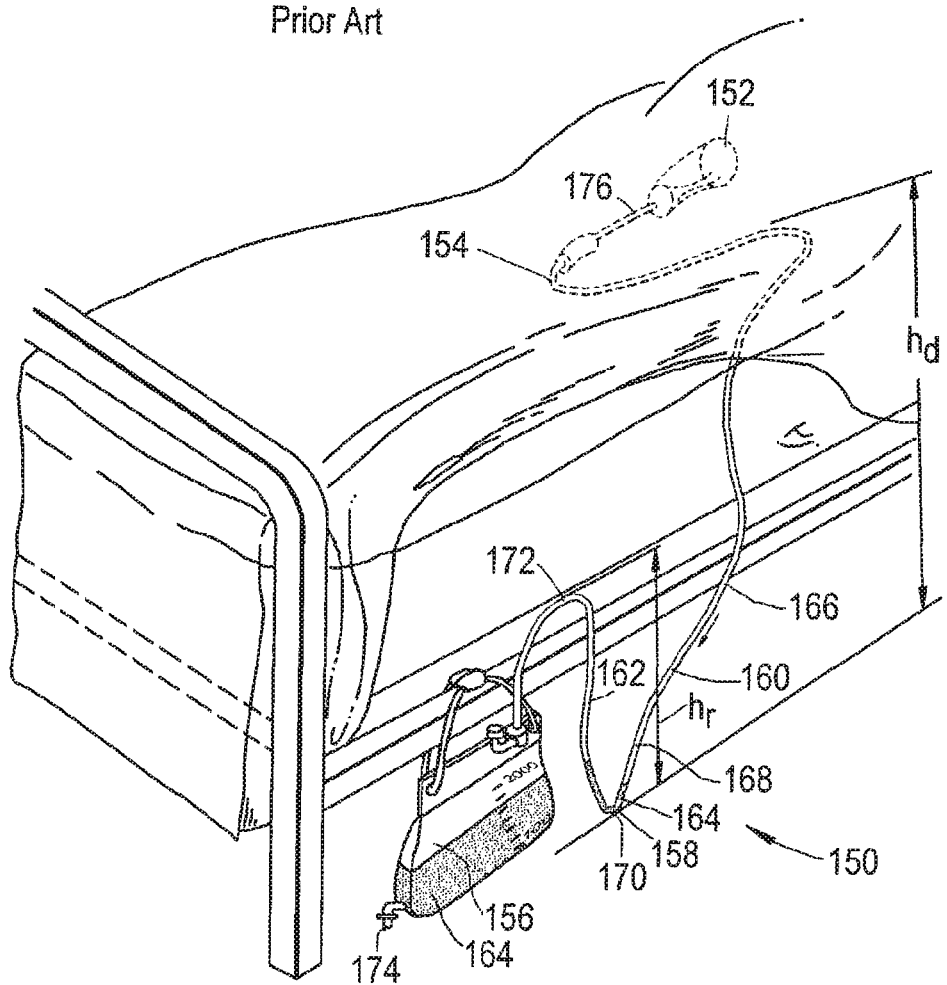

SYSTEMS AND METHODS FOR REMOVAL OF URINE

CROSS REFERENCE TO RELATED APPLICATIONS

The present application is a continuation of U.S. Ser. No. 14/037,371 filed on Sep. 26, 2013, which is a continuation of U.S. Ser. No. 12/669,494 filed on Jul. 5, 2010, now U.S. Pat. No. 8,568,387, which is a national phase of International Application No. PCT/IL2008/000986 filed on Jul. 16, 2008, which claims priority to Israeli Patent Application No. 184632 filed Jul. 16, 2007 and Israeli Patent Application No. 192774 filed Jul. 13, 2008 the entirety of which is incorporated herein by reference.

FIELD OF THE INVENTION

The present invention relates generally to systems and methods for removal of urine from a patient and more specifically to improved hygienic systems and methods for removal of urine from a catheterized patient.

BACKGROUND OF THE INVENTION

There are many situations in which a person, such as a hospitalized patient is unable to excrete waste products in a bathroom. Unconscious patients, paraplegics, some postoperative patients and incontinent patients all require means to continuously or semi-continuously remove urine without leakage thereof and risk of urinary tract infections (UTIs).

Many different types of urinary catheters have been devised to effectively remove urine from patients. For example:

GB1426429A, assigned to Simpla Plastics, describes a urinary collection apparatus comprising a collection bag and a tube connected at one end to the bag and having a connector cap for connection to a catheter at its other end, the tube comprising at least a portion which is of a material which is self-sealing when punctured by an instrument e.g. a hypodermic syringe, for withdrawing a sample of urine. The portion may comprise a sleeve of butadiene concentric with, and closely gripping the tube. The portion may form an integral part of the tube or the whole tube may be covered by a butadiene or an other self-sealing sleeve. The bag is provided with a drainage valve as disclosed in GB1310581 and has a one-way inlet valve. A graduated scale is provided on one face of the bag.

U.S. Pat. No. 3,861,396A to Bruckner describes means for eliminating a negative pressure problem, e.g. in a closed urinary system comprising a catheter, a downwardly extending tube and a collection bag. The tube has an internal coating of a hydrophilic polymer, preferably a 2-hydroxyethyl methacrylate polymer, or can be made completely of the hydrophilic polymer.

Bruckner describes there being a major problem with these systems, which is the build-up of negative pressures in the bladder for example, due to the build-up of the fluids columns in the various cannulae (lumens), e.g. see Vaillancourt U.S. Pat. No. 3,583,401.

This build-up is due to a combination of: a) closed system—which precludes the influence of atmospheric pressures which would break this column, and b) the surface tension of the tubing which acts to hold or retain the fluid in the tube.

Methods currently used to overcome this problem include: large bore drain tubing and the placing of a vent in the catheter connector. The former solution suffers from the limitation that the product is bulky and difficult to work with, whereas the latter has been demonstrated to only work for a very short period of time before the filter element gets clogged due to infestations, and/or hydrostatic pressures. The disclosure of '396 is concerned with a novel method which allows for the use of smaller bore tubing, as well as functioning over the life of the drainage system.

Briefly, '396 is concerned with using a hydrophilic tubing having an internal diameter of at least 0.2 inch to prevent capillary action as the connecting member (drainage tube) between the cannulae and collector. It has been found that a hydrophilic tube (having water-wetting properties) will not support a column of fluid even though a vacuum may be applied at one end.

U.S. Pat. No. 3,902,492, to Greenhalgh, describes a catheter for the continuous irrigation of the bladder which has a drainage tube for the removal of fluid from the bladder, an auxiliary axial bore extending through the wall of the drainage tube, and an irrigation tube extending from the axial bore beyond the tip of the catheter. The irrigation tube has a plurality of radial discharge outlets. During use, the irrigation tube curves around the bladder; fluid passes through the irrigation tube to provide a discharge spray and a turbulent flow of liquid in the bladder. This provides for a peripheral bladder irrigation which is an improvement over a single discharge point near the entry of a catheter into a bladder. The catheter also preferably has a second axial bore in its wall which terminates in an opening beneath a sheath of expandable material which can be inflated by fluid applied under pressure through the second axial bore, to secure the catheter in place.

U.S. Pat. No. 6,045,542, to Cawood et al., describes a urine collection bag having the basic features appearing in U.S. Pat. No. 4,449,971. The bag also includes an improvement in the form of an extendable drain tube that is normally retracted and retained in flat coiled condition against the front wall of the bag. The tube is biased into its coiled condition by the elastic memory of the thermoplastic material from which it is formed and, in a preferred embodiment, the flat coil is oval-shaped with its major axis extending generally vertically when the bag is worn. A retention strap attached to the front wall of the bag serves to hold the drain tube in its coiled condition against the bag's front wall. A valve is located at a distal end of the drain tube, which is used to control drainage. The location of the valve prevents spillage of residual urine upon recoil of the drain tube.

U.S. Pat. No. 7,094,220 to Tanghoj et al, describes a catheter assembly allowing for non-contaminated insertion of a catheter into a urinary canal. The assembly includes a package for the catheter and an applicator to be used for guiding the catheter into the urinary canal without touching the catheter by holding the catheter via walls of the applicator. The assembly further comprises clamping means for pressing the walls of the applicator into engagement with the catheter. The present invention further relates to an applicator with integrated clamping means to be used with the assembly.

The catheter or at least a section thereof may be provided with a hydrophilic surface. When treated with a liquid swelling medium, such a surface will provide an excellent lubrication for the insertion and also provide compatibility with the body tissue.

US2006189962A to Burtoft, describes a urinary drainage bag for draining urine from the navel as a result of a urinary diversion. The means include a urine collection bag, a reflux chamber attached to the collection bag for accommodating urine backflow and working out bubbles, a multi-size catheter tip extending upwardly from the reflux chamber for attachment to a transfer or catheter tube, a urine discharge opening adjacent the lower end of the collection bag for draining urine from the collection bag, and a fluid measurement scale imprinted on the front of the collection bag for measuring the amount of urine held within the urine collection bag.

The urinary drainage bag also includes a tether adjacent the upper end of the collection bag for conveniently hanging the collection bag, and a handle and mounting hook are also attached to the upper end of the collection bag for supporting the urinary drainage bag on a bed railing.

Thus, as will be noted from the publications hereinabove, the current state of the art is to use a catheter having at least part of the tubing thereof comprising a hydrophilic surface. Additionally, some of these publications relate to the negative pressure in the bladder, due to the build-up of the fluids columns in the various cannulae (lumens) as being a problem, which U.S. Pat. No. 3,861,396 sought to overcome.

It is to be noted, and as will be discussed hereinafter with regard to comparative FIGS. 1 and 2 relating to prior art arrangements, that there are still several major problems with the prior art arrangements which result in infection in catheterized patients both during catheterization and during the changing of the catheter arrangement.

Thus there is still a need to provide inexpensive, versatile urinary catheters, which allow for use over long periods of time with reduced risk of UTI.

Therefore, it is an object of some aspects of the present invention to provide hygienic systems and methods for collecting urine from a patient.

In preferred embodiments of the present invention, improved methods and novel apparatus are provided for collection of urine whereby the collection unit remains sterile throughout the collection time.

In other preferred embodiments of the present invention, a method and system are described for removing urine, under a constantly negative pressure, from a patient.

SUMMARY OF THE INVENTION

More particularly, the present invention provides an arrangement adapted for enhanced continuous flow of urine in a catheterized patient, the arrangement comprising a catheter tube having an inner diameter of less than six millimeters, said tube having an inner surface which is hydrophobic at least along a first segment thereof and adapted to provide a continuously negative fluid pressure therein In especially preferred embodiments of the present invention said tube is adapted to provide a continuously negative fluid pressure of less than 50 cm water or the equivalent thereof.

By the term "or the equivalent thereof" it is intended to denote that there are many ways of measuring pressure and that the following are considered to be substantially equivalent.

50 cm of water
0.05 Bar
50 Milli Bar
0.049 Atmosphere
3.75 cm Mercury
1.476 Inches Mercury
0.05 Kilogram/cm squared
5 Kilopascal
0.725 PSI.

As stated, said tube has an inner surface which is hydrophobic at least along a first segment thereof, and in preferred embodiments of the present invention said tube is disposed to provide a down-corner portion proximal to a first end thereof and a riser portion proximal to a second end thereof and said tube has an inner surface which is hydrophobic at least along said down-corner portion thereof.

In especially preferred embodiments of the present invention, the inner surface of said tube is hydrophobic along its entire length.

Thus said tube can be constructed of a hydrophobic material or the inner surface thereof can be coated with a hydrophobic material.

In preferred embodiments of the present invention, said tube is adapted for fluid conveying attachment to a catheter and for attachment to a urine collection bag.

In some preferred embodiments of the present invention said tube is adapted for one time, one-way, non-releasable attachment to a catheter.

In other preferred embodiments of the present invention said tube is adapted for non-releasable attachment to a urine collection bag.

In some preferred embodiments of the present said tube is non-releasably attached to a urine collection bag.

In other preferred embodiments of the present invention said tube is non-releasably attached to a catheter.

Also provided according to the present invention is a method for enhanced continuous flow of urine in a catheterized patient comprising:

a. providing an arrangement comprising a hydrophobic catheter tube having an inner diameter of less than six millimeters, said tube having an inner surface which is hydrophobic at least along a first segment thereof and being arranged to provide a continuously negative fluid pressure therein; and b. non-releasably attaching said hydrophobic catheter tube to said urinary catheter unit, and releasably attaching said tube to a urine collection bag, said catheter unit being adapted to continuously remove fluid from the patient and to convey said fluid into said tube under a continuously negative fluid pressure.

The invention also provides, a system for enhanced continuous flow of urine in a catheterized patient comprising:

a. a catheter tube having an inner diameter of less than six millimeters, said tube having an inner surface which is hydrophobic at least along a first segment thereof and being adapted to provide a continuously negative fluid pressure therein;

b. a urinary catheter unit, said catheter unit being adapted to convey said fluid through said tube; and c. a urine collection apparatus releasably and fluidly connected to said tube.

In preferred embodiments of said aspect of the invention, said tube is provided with a first connector for attachment to a catheter and at a second connector for attachment to a urine collection bag.

In preferred embodiments of the present invention said tube has an inner diameter of less than five millimeters.

In especially preferred embodiments of the present said tube has an inner diameter of less than four millimeters.

Preferably said tube is adapted for non-releasable attachment to a catheter.

In some preferred embodiments of the present invention said tube is non-releasably attached to a catheter.

Preferably, said tube comprises at least one hydrophobic material selected from a thermoplastic elastomeric material, a thermoplastic material, a curable elastomeric material, a polyimide resin; an elastomer and mixtures or blends thereof.

In said preferred embodiments, said material is preferably selected from at least one of polypropylene (PP), polyvinyl chloride (PVC), polyurethane (PU), polyethylene (PE), EVA, latex, and Kraton™ and mixtures or blends thereof.

In some preferred embodiments of the present invention said tube is connected to a urinary catheter unit, said catheter unit being constructed and adapted to remove fluid from the patient and to convey said fluid into said tube.

In preferred embodiments of the arrangement of the present invention said tube is disposed to provide a down-corner portion proximal to a first end of said tube and a riser portion proximal to a second end of said tube.

Preferably, said tube is configured and adapted to provide a continuous head of fluid from the patient to the down-corner portion of the tube.

In especially preferred embodiments of the present invention said tube is configured and adapted to remain full of urine during operation.

As stated hereinbefore, in preferred embodiments the arrangement is such that a negative height difference between said second end and said patient is arranged to provide said continuously negative fluid pressure of between 5-50 cm water or the equivalent thereof.

As will be discussed hereinafter, in especially preferred embodiments of the present invention, said tube is adapted to maintain a meniscus head of fluid along at least a portion of said tube without interruption and in the most preferred embodiments said tube is adapted to be continuously sterile over a period of time as a result of a meniscus head of fluid moving from said patient to said urine collection bag along said tube without interruption.

In especially preferred embodiments of the present invention the apparatus and arrangement of the present invention is adapted to prevent urinary tract infections in the patient as a result of the continuous negative fluid pressure in the tube and the other features described and claimed herein.

Furthermore, said arrangement is adapted to continuously remove liquid from said patient so as to substantially prevent the accumulation of a bolus in the bladder of the patient.

As will be realized, in its preferred embodiments, said arrangement is constructed and operative to provide a continuously negative pressure in the tube and to the bladder of the patient.

A further aspect of the present invention relates to the use of a hydrophobic catheter tube having an inner diameter of less than six millimeters in the construction of an arrangement for enhanced continuous flow of urine in a catheterized patient, wherein said tube has an inner surface which is hydrophobic at least along a first segment thereof and being arranged to provide a continuously negative fluid pressure therein.

In another aspect of the present invention, there is provided a catheterization kit comprising a hydrophobic catheterization tube having an inner diameter of less than 6 mm and provided with a first connector for non-releasable attachment to a catheter and with a second connector for releasable attachment to a urine collection bag and a catheter.

In preferred embodiments of the present invention said catheter tube will preferably have a bore to wall thickness ratio of about 3:1.

In some preferred embodiments of the present invention the tube will be provided with graduated markings along its length such that each marking will corresponding to a specific volume thereby providing the ability for manual readings in the initial stages of flow, especially when the flow is very low and before the tube is full.

In some preferred embodiments of the present invention there will be provided a non-return valve on the collection bag where the urine enters said bag, so that there will be no back-flow of contaminated urine into the tube from the collection bag and so that when the pipe is disconnected there will be no spillage of urine from the collection bag.

In other preferred embodiments of the present invention there will be provided an air valve in the tube in the region where connection is made to the collection bag, thereby preventing the creation of a vacuum when urine samples are taken at a sample port situated in the region of the catheter connection.

In especially preferred embodiments of the present invention the internal surface of the tube is highly polished in order to enhance the maintenance of the meniscus.

While the invention will now be described in connection with certain preferred embodiments in the following examples and with reference to the attached figures so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

BRIEF DESCRIPTION OF THE DRAWINGS

The present invention will be more fully understood from the following detailed description of the preferred embodiments thereof, taken together with the drawings, in which:

FIG. 1b is a simplified pictorial illustration showing a prior art hydrophilic urinary catheter system for collecting urine from a catheterized patient;

DETAILED DESCRIPTION OF PREFERRED EMBODIMENTS

In order to illustrate the specific advantages of the present invention, a few of the problems associated with prior art urinary catheter systems are now described.

Figure 1A:
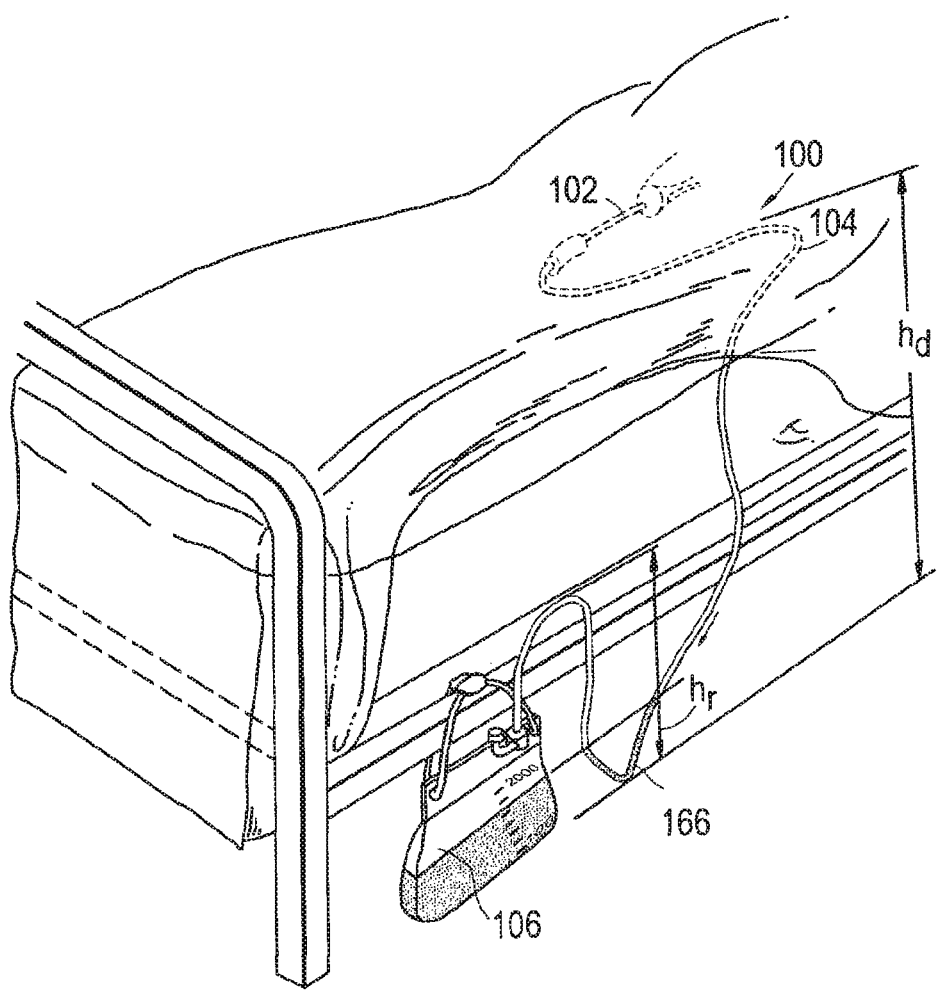
FIG. 1a is a simplified pictorial illustration showing a prior art hydrophilic urinary catheter system for collecting urine from a catheterized patient.

Reference is made to FIG. 1a, which is a simplified pictorial illustration showing a hydrophilic prior art urinary catheter system for collecting urine from a catheterized patient.

System 100 comprises a urinary catheter unit 102 connected to a tube 104. The tube is typically of a hydrophilic material, as exemplified in U.S. Pat. No. 3,861,396A. The downwardly extending tube normally hangs over the edge of a bed and is fluidly connected to a collection bag 106. The collection bag is typically located on the floor or closely hanging thereabove. The hydrophilic surface of tube 104 normally allows urine to trickle down a surface thereof without building up a negative pressure.

Figure 1C:
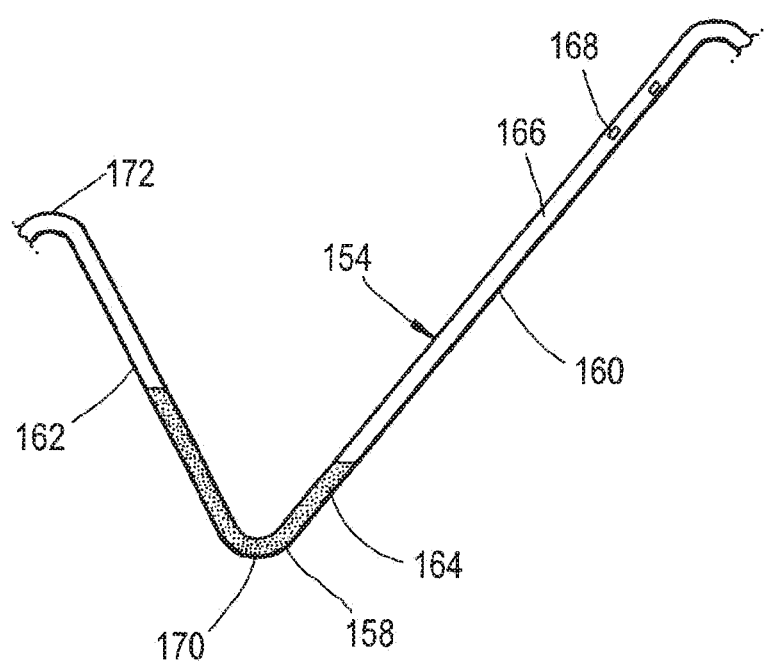
FIG. 1c is a detailed view of part of the arrangement seen in FIG. 1B.

Reference is now made to FIGS. 1b and 1c, which is a simplified pictorial illustration showing a prior art hydrophilic urinary catheter system 150 for collecting urine from a catheterized patient. System 150 comprises a urinary catheter 176 connected to a tube 154. The downwardly extending tube normally hangs over the edge of a bed and is fluidly connected to a collection bag 156. The collection bag 156 is typically located on the floor or closely hanging thereabove.

The prior art tubes typically are of a diameter greater than 6 mm and as such urine drops simply fall through the tube until reaching the loop 158 thereof.

In such an arrangement, urine 164 typically accumulates in a loop 158 of the tube connecting between a down-coming portion 160 thereof, having a vertical height hd (the difference in height from the bladder of the patient to the lowest point 170 of down-coming portion 160) and a riser portion 162 thereof. The riser portion has a vertical height, hr, measured from lowest point 170 to highest point 172.

As urine 164 accumulates in loop 158, the riser portion and down-corner portion of tube 154 gradually collect urine therein. Normally, at a pseudo-steady state there is a constant "U-shaped" accumulation of urine 164 in the tube and an air trap 166 above the urine in the riser section. This air trap 166 may contain contaminated air and lead to the accumulation of bacterial or other colonies 168 on the inner surface of the tube. These colonies or bacteria/other microbes therefrom may then be drawn into the bladder under various circumstances as the height of the accumulation of urine 164 in the tube increases due to the positive pressure in the tube between the bladder 152 and the beginning of loop 158 and induces a urinary tract infection (UTI).

In many medical centers, the "U-shaped" urine accumulation is milked out of the tube 154 and air enters from the collection apparatus 156 into the tube 154. Again, this air may contain microbial or other contaminants and may induce UTI in the patient.

It is to be understood that the collection bag is usually provided with a tap 174 from which urine 164 is emptied at least once a day. Upon emptying of the urine 164, air from the surroundings is sucked into and enters the collection bag 156, and since air normally contains bacteria and since the bag is a warm, humid environment, bacteria naturally breeds within the bag, which bag is not changed within a period of between 2 weeks and a month.

When the "u-shaped" urine accumulation is milked out of the tube 154, the bolus of urine which is normally formed in the bladder, flows through the tube, and creates a suction from the bladder to the tube to the urine collection bag, and so the infected air from the urine collection bag is often sucked into the bladder causing infection.

Figure 2:
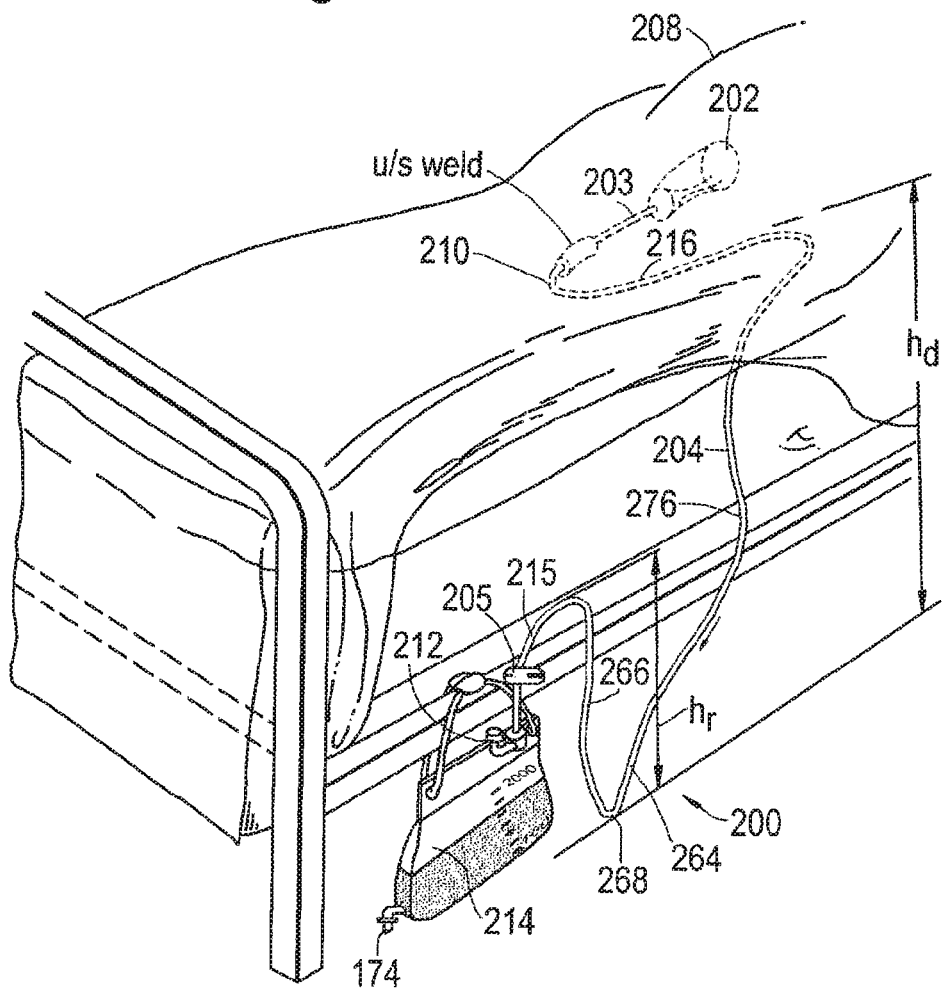
FIG. 2 is a simplified pictorial illustration showing a urinary catheter arrangement, in accordance with an embodiment of the present invention.
Figure 2A:
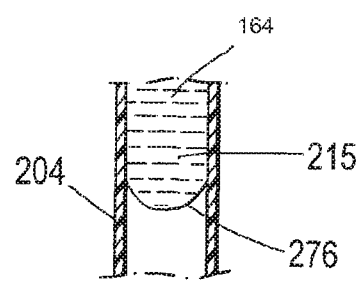
FIG. 2a is an enlarged cross-section of the tube of the present invention.

Turning now to FIGS. 2 and 2a, there is seen a simplified pictorial illustration showing a urinary catheter arrangement 200, in accordance with an embodiment of the present invention.

The arrangement of the present invention is arranged for enhanced continuous flow of urine in a catheterized patient and for preventing urinary tract infections in the patient, the arrangement comprises a hydrophobic catheter tube 204 having a diameter of less than six millimeters, the tube being arranged to provide a continuously negative fluid pressure of less than 50 cm equivalent of water therein as a result of a meniscus 276 forming at the beginning of a flow of urine 164 from the bladder 202 of the patient as a result of the narrowness of the tube and the repulsion of the urine from the hydrophobic surfaces of the tube, whereby during operation, the tube is always full of urine.

As a result, a natural negative pressure builds up in the tube which serves to continuously suction urine from the bladder 202 in a closed system, keeping the bladder empty resulting in a steady flow which does not allow for air spaces and bacterial build-up in the tube in the area adjacent the bladder.

The difference in the length of the down-coming portion 264 to the riser portion 266 is normally less than 60 cm, preferably less than 50 cm. This difference in height below the level of the bladder 202 of the patient and the collection bag 214, is adapted to induce a negative pressure in the bladder of the patient, as will be explained in more detail hereinbelow.

Typically, tube 204 has a diameter of less than five millimeters. Preferably, the diameter is less than four millimeters.

Tube 204 comprises at least one hydrophobic material preferably selected from a thermoplastic elatomeric material, a thermoplastic material, a curable elastomeric material, a polyamide resin; an elastomer and mixtures or blends thereof.

The tube may be made of the hydrophobic material or internally lined with the hydrophobic material as is known in the art. The material may be selected from, but is not limited to, at least one of polypropylene (PP), polyvinyl chloride (PVC), polyurethane (PU), polyethylene (PE), EVA, latex, and Kraton™ and mixtures or blends thereof.

Arrangement 200 is constructed and operative to remove urine from a bladder 202 of a patient 208, with the tube being preferably non-releasably connected at a first end 210 to a urinary catheter 203, and the catheter 203 being constructed and operative to remove fluid from the bladder of the patient and to convey urine into tube 204.

The arrangement of the present invention comprises tube 204 being releasably and fluidly connected at a second end 212 to a urine collection apparatus 214.

Tube 204 is further provided with clamp means 205 which are used to close the tube 204 when the urine collection apparatus 214, e.g., a urine collection bag, is to be replaced.

As will be realized, by using clamp means 205, the negative pressure in tube 204 is retained and thus the urine collection bag can be replaced at shorter intervals than that of the replacement of the tube 204 and the attached catheter 203.

The tube of the present invention is adapted to provide a continuous head 215 of urine, led by meniscus 276 from the urinary catheter 203 into the down-coming portion 264 of tube 204. A difference in the height of head 215 above the height of second end 212 provides a negative pressure in the tube.

As will be understood, a negative pressure arises when there is a hydrostatic head as shown, due to a flow of urine in the narrow hydrophobic tube 204 below the vertical level of the urinary catheter 203. This negative pressure exerts a sucking action on the bladder 202 and prevents the formation of a bolus of urine therein.

Typically, the arrangement comprises tube 204 disposed to provide a down-coming portion 264 proximal to first end 210 and riser portion 266 proximal to the second end 212.

The arrangement normally comprises a continuous head of fluid 216 from bladder 202 to the down-corner portion 264 of tube 204.

Arrangement 200 provides a negative height difference between second end 212 and bladder 202 to provide said continuously negative fluid pressure of between 5-50 cm water.

Contrary to prior art systems 100, 150, there is no "U shaped" accumulation of urine 164 in the tube and consequentially no air trap 166 between loop 268 and the urinary catheter 203. The arrangement of the present invention provides a constant head of urine 164 in tube 204, which prevents air from entering bladder 202.

Additionally, the negative pressure in arrangement 200 of the present invention prevents the creation of a bolus of urine (not shown) in bladder 202.

As was explained hereinabove, the tube is disposed to provide a continuously negative fluid pressure of between 5-50 cm water; in some cases between 10-40 cm water; and in other cases, a negative fluid pressure of between 25-40 cm water or the equivalent thereof using a different pressure scale as set forth above.

It should be understood that the bladder typically excretes urine, though in some cases, such as during operative procedures the bladder may release a fluid comprising at least one of urine and blood.

In some cases, catheterized patient 208 may suffer from a UTI prior to being connected to the arrangement of the present invention.

Urine collection apparatus 214 may be a bag or other means known in the art.

The arrangement may be constructed and operative to continuously remove urine and/or other liquids 164 from bladder 202 so as to substantially continuously prevent the accumulation of a bolus in the bladder.

According to some embodiments, arrangement 200 is constructed and operative to provide a continuously negative pressure in bladder 202. Normally, the negative pressure is less than 50 cm equivalent of water therein or the equivalent thereof.

In preferred embodiments, first end 210 is connected via a non-releasable permanent connector (not shown) to catheter 203. The catheter 203, and tube 204 may be integrally formed and adapted for use over a period of time of up to one month, or in some cases, a fortnight.

Figure 3:
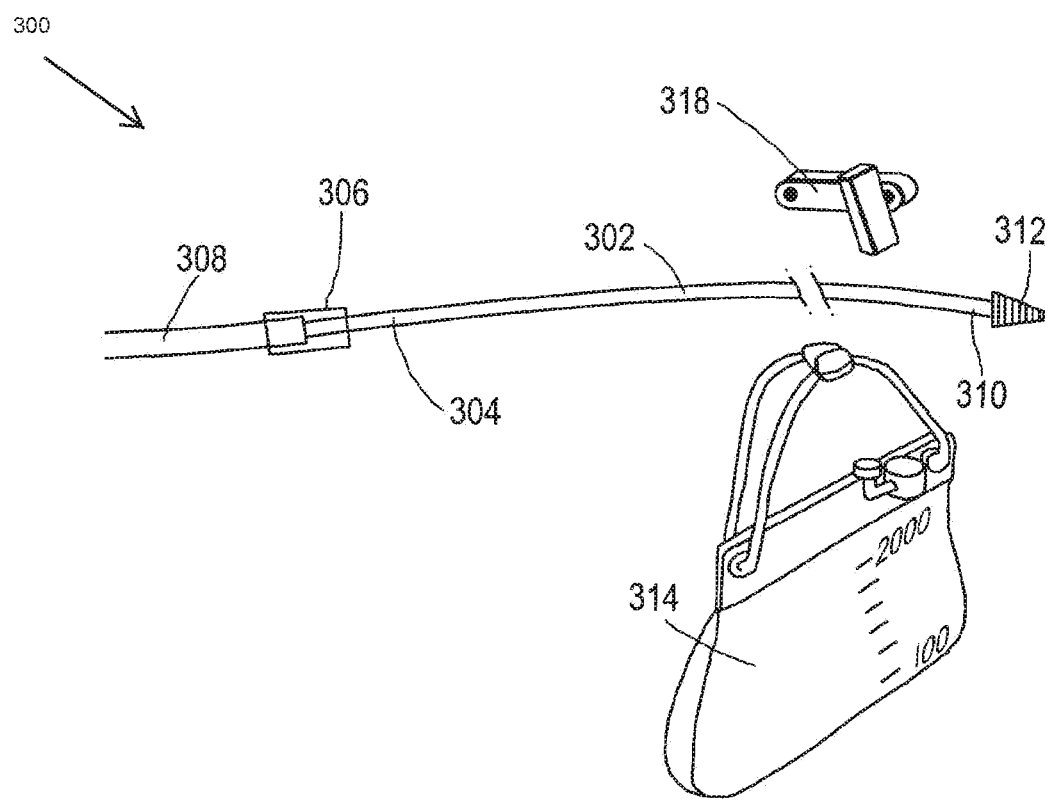
FIG. 3 is a perspective view of a catheterization kit comprising a catheterization tube provided with means for attachment to a catheter and for attachment to a urine collection bag and a catheter.

FIG. 3 shows a catheterization kit 300 comprising a hydrophilic catheterization tube 302 having a diameter of less than 6 mm and provided at a first end 304 with means 306 for permanent non-releasable attachment to a catheter 308 and at a second end 310 for releasable attachment 312 to a urine collection bag 314 and a segment of a catheter 308.

Catheterization tube 302 is further provided with clamping means 318 to facilitate the removal and replacement of bag 314 without disturbing negative pressure within the tube 302 and thereby preventing the possibility of infection from the tube to the bladder (not shown) and to prevent urine leakage.

As will be realized the catheter unit or at least a part of the catheter unit and or the tube may be made from silicone or from a thermoplastic elastomeric material, other thermoplastic materials, curable elastomeric materials, polyamide resins or elastomers or any mixture thereof, i.e. the group may comprise materials like, PVC, PU, PE, EVA, latex, and/or Kraton™.

In addition in preferred embodiments of the present invention said tube is provided with internal ridges so as to prevent the blockage thereof in the event of an inadvertent kinking of the tube or pressure thereon.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

The invention claimed is:

1. A catheter tube comprising:
two ends, adapted for connecting to a catheter at a first end and to a urine collection bag at a second end, said catheter tube having an inner diameter of less than six millimeters and having an inner surface which is hydrophobic and polished, wherein said catheter tube is arranged and configured to continuously provide negative pressure in said tube in order to convey a column of fluid held by a meniscus of said column of fluid within said catheter to said collection bag and prevent the formation of an air trap within said catheter tube and prevent a formation of a bolus of urine within a bladder of a patient; and,
a clamp disposed on the catheter tube between the first end and the second end and configured to maintain the negative pressure within said catheter tube when said catheter tube is disconnected from the urine collection bag.

2. The catheter tube of claim 1, wherein said catheter tube is disposed to provide a continuous negative fluid pressure representing less than 50-centimeter water.

3. The catheter tube of claim 1, wherein said catheter tube is disposed to provide a continuous negative fluid pressure representing between 10-centimeter to 40-centimeter water.

4. The catheter tube of claim 1, wherein said catheter tube is disposed to provide a continuous negative fluid pressure representing between 25-centimeter to 40-centimeter water.

5. The catheter tube of claim 1, wherein said clamp is disposed proximate said second end of said catheter tube.

6. The catheter tube of claim 1, wherein said tube includes a hydrophobic material including at least one of: a thermoplastic elastomeric material, a thermoplastic material, a curable elastomeric material, a polyamide resin, and an elastomer.

7. The catheter tube of claim 6, wherein said hydrophobic material is selected from at least one of: polypropylene (PP), polyvinyl chloride (PVC), polyurethane (PU), polyethylene (PE), EVA, latex, and Kraton™.

8. The catheter tube of claim 1, wherein said catheter tube comprises an ascending portion having a first vertical height and a descending portion having a second vertical height, wherein a difference between said first vertical height and said second vertical height induces the negative pressure.

9. A catheter tube comprising:
two ends, adapted for connecting to a catheter at a first end and to a urine collection bag at a second end, said catheter tube having an inner diameter an inner diameter of from four millimeters to six millimeters and having an inner surface which is hydrophobic and polished, wherein said catheter tube is arranged and configured to continuously provide negative pressure in said tube in order to convey a column of fluid held by a meniscus of said column of fluid within said catheter to said collection bag and prevent the formation of an air trap within said catheter tube and prevent a formation of a bolus of urine within a bladder of a patient; and,
a clamp disposed on the catheter tube between the first end and the second end and configured to maintain the negative pressure within said catheter tube when said catheter tube is disconnected from the urine collection bag.

10. The catheter tube of claim 9, wherein said catheter tube is disposed to provide a continuous negative fluid pressure representing less than 50-centimeter water.

11. The catheter tube of claim 9, wherein said catheter tube is disposed to provide a continuous negative fluid pressure representing between 10-centimeter to 40-centimeter water.

12. The catheter tube of claim 9, wherein said catheter tube is disposed to provide a continuous negative fluid pressure representing between 25-centimeter to 40-centimeter water.

13. The catheter tube of claim 9, wherein said clamp is disposed proximate said second end of said catheter tube.

14. The catheter tube of claim 9, wherein said tube includes a hydrophobic material including at least one of: a thermoplastic elastomeric material, a thermoplastic material, a curable elastomeric material, a polyamide resin, and an elastomer.

15. The catheter tube of claim 14, wherein said hydrophobic material is selected from at least one of: polypropylene (PP), polyvinyl chloride (PVC), polyurethane (PU), polyethylene (PE), EVA, latex, and Kraton™.

16. The catheter tube of claim 9, wherein said catheter tube comprises an ascending portion having a first vertical height and a descending portion having a second vertical height, wherein a difference between said first vertical height and said second vertical height induces the negative pressure.

* * * * *